(12) United States Patent
Foldvari et al.

(10) Patent No.: US 8,945,529 B2
(45) Date of Patent: Feb. 3, 2015

(54) BIPHASIC LIPID-VESICLE COMPOSITIONS

(75) Inventors: Marianna Foldvari, Kitchener (CA); Praveen Kumar, Saskatoon (CA); John M. Docherty, Richmond Hill (CA)

(73) Assignee: Helix BioPharma Corporation, Aurora (CA)

(*) Notice: Subject to any disclaimer, the term of this patent is extended or adjusted under 35 U.S.C. 154(b) by 205 days.

(21) Appl. No.: 12/532,752

(22) PCT Filed: Mar. 27, 2008

(86) PCT No.: PCT/CA2008/000563
§ 371 (c)(1),
(2), (4) Date: Jan. 8, 2010

(87) PCT Pub. No.: WO2008/119160
PCT Pub. Date: Oct. 9, 2008

(65) Prior Publication Data
US 2010/0196453 A1 Aug. 5, 2010

Related U.S. Application Data

(60) Provisional application No. 60/909,324, filed on Mar. 30, 2007.

(51) Int. Cl.
| | |
|---|---|
| A61K 38/21 | (2006.01) |
| A61K 9/127 | (2006.01) |
| A61K 38/00 | (2006.01) |
| A61K 9/00 | (2006.01) |
| A61K 31/198 | (2006.01) |
| A61K 47/18 | (2006.01) |
| A61K 9/10 | (2006.01) |
| A61K 9/107 | (2006.01) |

(52) U.S. Cl.
CPC ............. *A61K 9/127* (2013.01); *A61K 9/0034* (2013.01); *A61K 9/1277* (2013.01); *A61K 31/198* (2013.01); *A61K 38/21* (2013.01); *A61K 47/183* (2013.01); *A61K 38/212* (2013.01); *A61K 9/10* (2013.01); *A61K 9/1075* (2013.01)
USPC ........................ 424/85.7; 424/450; 514/21.2

(58) Field of Classification Search
None
See application file for complete search history.

(56) References Cited

U.S. PATENT DOCUMENTS

| | | |
|---|---|---|
| 5,358,708 A | 10/1994 | Patel |
| 6,264,990 B1 | 7/2001 | Knepp et al. |
| 6,656,499 B1 | 12/2003 | Foldvari et al. |

FOREIGN PATENT DOCUMENTS

| | | |
|---|---|---|
| JP | 2006-525280 | 11/2006 |
| WO | WO95/03787 A1 | 2/1995 |
| WO | WO99/11247 A1 | 3/1999 |
| WO | WO-2004/096263 | 11/2004 |
| WO | WO-2005/087201 | 9/2005 |

OTHER PUBLICATIONS

Stellato, G., 'Intralesional recombinant alpha 2b interferon in the treatment of human papillomavirus-associated cervical intraepithelial neoplasia', *Sexually Transmitted Diseases*, vol. 19, No. 3, pp. 124-126 (1992).
Yliskoski, M. et al., 'Topical treatment with human leukocyte interferon of HPV 16 infections associated with cervical and vaginal intraepithelial neoplasias', *Gynecologic Oncology*, vol. 36, No. 3, pp. 353-357 (1990).
Mantripragada, "A lipid based depot (DepoFoam technology) for sustained release drug delivery", Prog Lipid Res., 2002, 41(5):392-406.
Qui et al., "Multivesicular liposome formulations for the sustained delivery of interferon alpha-2B", Acta Pharmacol Sin., 2005, 26(11):1395-1401.
Wang, "Instability, stabilization, and formulation of liquid protein pharmaceuticals", Int J Pharm., 1999, 185(2):129-188.

*Primary Examiner* — Robert Landsman
*Assistant Examiner* — Bruce D Hissong
(74) *Attorney, Agent, or Firm* — Foley & Lardner LLP

(57) ABSTRACT

A biphasic lipid vesicle composition for treating cervical displasia by intravaginal delivery. The composition includes a suspension of lipid-bilayer vesicles having entrapped therein, an oil-in-water emulsion, human interferon alpha-2b and L-methionine, the composition having an interferon alpha-2b specific activity of between about 1-10 MIU (million international units) per gram composition, and between 0.01 to 0.5 weight percent L-methionine. In the treatment method, the composition is administered at a dose of between about 1-20 MIU interferon alpha-2b, and this dose is administered at least 3 days/week, for a period of at least 4 weeks.

9 Claims, 3 Drawing Sheets

BIPHASIC LIPID-VESICLE COMPOSITIONS

This application is the National Stage of International Application No. PCT /CA2008/000563 filed on Mar. 27, 2008, which claims the benefit of U.S. Provisional Application No. 60/909,324 filed on Mar. 30, 2007, both of which are incorporated herein in their entirety by reference.

FIELD OF THE INVENTION

The present invention relates a biphasic lipid-vesicle composition and method for treating cervical displasia by intravaginal delivery.

BACKGROUND OF THE INVENTION

Of the estimated 55 million Pap smears performed each year in the United States, more than 5% are reported as abnormal (ALTS study 2003). An estimated 800,000 women each year present with low-grade squamous intraepithelial lesions (LSIL) (Jones, BA, Davey DD. Quality management in gynaecologic cytology using interlaboratory comparison. Arch Pathol Lab Med 2000; 124(5):672-81).

These lesions will either progress with time to CIN 2-3 or invasive cancer, especially in women that present with the high-risk HPV-subtype, or regress with time in the absence of treatment. Of women diagnosed with LSIL, 25% will progress to cervical intraepithelial neoplasia (CIN) grade 2 or 3, 22-32% will have persistent CIN 1 and approximately 50%-70% will experience spontaneous regression of LSIL within 2 years (ALTS group 2003, Östör AG Natural history of cervical intraepithelial neoplasia: a critical review. Int. J. Gynecol Pathol 1993; 12:186-92). Approximately 75% will experience spontaneous regression within 5 years.

The cytologic LSIL definition of the Bethesda System is different from the Munich classification system used in Germany and throughout the EU. LSIL corresponds to condyloma or CIN 1 in the Bethesda System. In the Munich classification these findings are represented in the Pap groups II W-III D. However, it should be noted that in group III D also patients with colposcopic diagnosis of CIN 2 (moderate dysplasia) are included.

At present, there is no immediate therapy available for women with HPV presenting with LSIL. Once a low-grade abnormal Pap smear has been detected, the patient and the clinician are left with the choice of either repeating it one or more times, or proceeding to colposcopy. Colposcopy is often accompanied by biopsy. Based on the findings of the colposcopy and biopsy, treatment options include conization, cryotherapy or laser treatment. Women who have undergone such treatment options may carry an increased risk of abortion and premature labor.

There are a number of clinical trials that have been published that describe interferons to be effective against a variety of HPV cervical infections. Studies on the use of interferons for the treatment of cervical intraepitehial neoplasia report cure rates between 0-100%. These variations most likely reflect differences in dosage, duration of treatment, mode of application, study design, severity of disease, and measures of efficacy.

In an open study, Penna et al. (1994) (Penna C, Fallan MG, Gordigiani R et al., Intralesional beta-interferon treatment of cervical intraepithelial neoplasia associated with human papillomavirus infection, Tumori 1994; 80:146-150) reported 80% lesion regression and 51% reversion of HPV type 16/18 to normal following daily intra-perilesionally application into the cervix in women with CIN associated with HPV infection of 3 MIU of IFN beta for 3 weeks. Similarly, in an open pilot study, Katesmark et al. (1999) (Katesmark M., Coulter Smith S., Reynolds K., Lawton F. A pilot study of the efficacy and tolderablity of intralesional recombinant human beta interferons in cervical intraepithelial neoplasia. Ann Acad Singapore 1999; 28(6)775-7) showed a 73% histology complete response rate of CIN when IFN was injected into the transformation zone.

Schneider et al. (1995) (Schneider A, Grubert T, Kirchmayr R, Wagner D, Papendick U, Schlunck G. Efficacy trial of topically administered Interferon gamma-1b gel in comparison to laser treatment in cervical intraepithelial neoplasia. Arch Gynecol Obstet 1995; 256:75-83) reported a 42% complete response, 42% partial response following IFN-gamma 1b gel therapy in women with CIN. In this study, patients with CIN II responded better compared with CIN III. It is also of interest to note that smokers showed a significantly lower cure rate when compared to non-smokers.

Zarcone at al. (1995) (Zarcone R., Bellini P., Cardone G., Cardone A. Treatment of cervix condylomata with alpha-IFN leucocytar. Clin Exp Obst Gyn 1995; 22(4):326-9) have reported success in a small, 12-patient study with combined intramuscular and topical alpha-IFN therapy in the treatment of CIN I and II, in HPV+ women. The administration of intramuscular doses of up to 3 MIU daily IFN for 3 weeks, combined with intravaginal application of an unspecified dose of IFN cream during the last two weeks of treatment, resulted in a complete response in 7 patients, partial response in 4 patients, and no response in 1 patient.

Syed et al. (1998) (Syed TA, Ahmadpour A. Human leukocyte derived interferon-a in hydrophilic gel for the treatment of intravaginal warts in women: a placebo-controlled, double-blind study. Intl J STD and AIDS 1998; 9:769-772) demonstrated that 16 MIU daily dose of a hydrophilic gel of interferon alpha administered intravaginally for 5 consecutive days per week over a 4-week treatment period was significantly more effective than placebo at curing vaginal warts. While these studies show that interferon therapy is effective in treating CIN associated HPV infections as measured by colposcopy confirmed by cytological and histological examination of random biopsies, none of these studies examine the HPV status post therapy.

Based on various limitations in these studies, a non-invasive therapy that could reverse the abnormal cytology during the early stages of the disease process and diminish or eradicate HPV presence would provide a significant benefit to the healthcare system and the physical and emotional well-being of many young women.

SUMMARY OF THE INVENTION

In one aspect, the invention includes a biphasic lipid vesicle composition for treating cervical dysplasia by intravaginal delivery. The composition includes a suspension of lipid-bilayer vesicles having entrapped therein, an oil-in-water emulsion, human interferon alpha-2b and methionine, the composition having an interferon-alpha-2b specific activity of between about 1-10 MIU (million international units) per gram composition and between 0.01 to 0.5 weight percent methionine.

The composition, which may be in a cream form, contains in particular embodiments, interferon alpha-2b at an specific activity between 1 and 3 MIU human interferon alpha-2b per gram composition and between 0.01 to 0.5 weight percent L-methionine In another aspect, the invention includes a method of treating cervical dysplasia in the subject by administering the above composition intravaginally to the subject, at a dose of between 1-20 MIU interferon alpha-2b, and repeating the dosing at least 3 days/week, for a period of at least 4 weeks.

These and other objects and features of the invention will be more fully appreciated when the following detailed description of the invention is read in conjunction with the accompanying drawings.

DETAILED DESCRIPTION OF THE INVENTION

Figure 1:
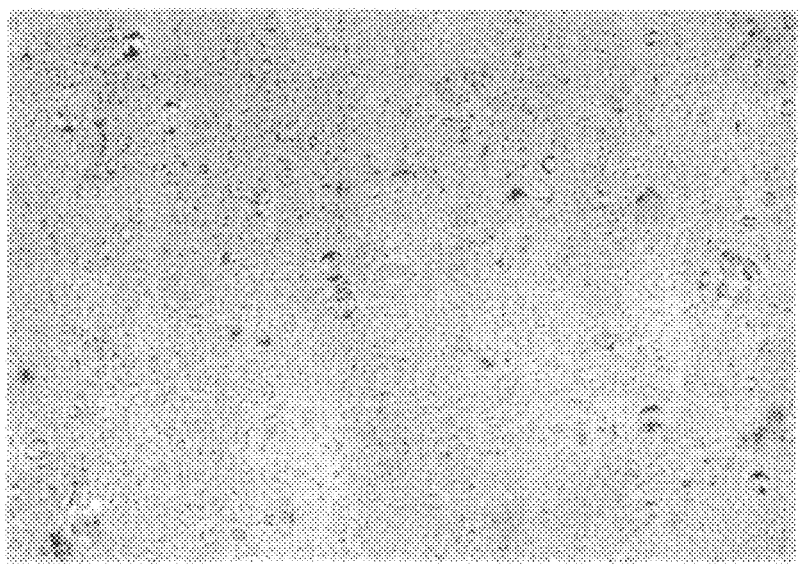
FIG. 1 is a scanned image of multilamellar lipid vesicles in the composition of the invention, prepared using an anhydrous plastic proliposome gel method.

I. Biphasic Liposome Composition and Method of its Preparation

The invention relates to a lipid-bilayer or liposome or lipid vesicle composition for use in delivering an interferon, e.g., interferon alpha-2b by transmucosal delivery, e.g., by intravaginal administration, particularly in the treatment of cervical dysplasia.

A preferred method of preparing a multilamellar lipid vesicle of the invention is as follows. An oil and a consistency enhancer are admixed. Separately, water and a surfactant are admixed. A water-soluble antimicrobial agent, for example methyl paraben or propylparaben, a buffering agent, such as phosphates, and a chelating agent, such as EDTA, can also be dissolved in the water. These are heated gently, say to about 70° C., and then admixed and homogenized with the oil and consistency enhancer. This results in formation of an emulsion with water as the continuous phase and the oil and consistency enhancer as the dispersed phase. It is desirable that the oil droplets shall be less than about 1 μm, especially less than about 0.5 μm, in diameter and if necessary the emulsion can be subjected to additional shear or to sonication to reduce the size of the droplets.

Separately there is prepared an anhydrous proliposome gel by admixing phospholipid, glycolipid and/or ceramide and a pharmaceutically acceptable hydrophilic solvent, e.g., propylene glycol, and heating them to form a melt. In the melt there may also be incorporated a material to enhance the strength of the lipid bilayers, for example cholesterol, a material to enhance penetration, for example monolauroyllysine and a material to impart a charge to the lipid bilayers, for example stearic acid. A small amount of an antioxidant, for example ascorbyl palmitate, butylated hydroxytoluene or butylated hydroxyanisole can be incorporated in the melt. The aqueous emulsion is added to the melt and the various components are subjected to agitation which results in formation of the desired multilamellar lipid vesicles having in the central core compartment an aqueous emulsion containing the oil and consistency enhancer as the dispersed phase.

A water-soluble biologically active material, and in particular, human interferon alpha-2b can be incorporated in solution in the aqueous phase of the emulsion, as discussed below. The interferon alpha-2b is incorporated at into the aqueous phase to form a final composition having a specific activity of between 1-10 MIU per gram composition. The composition is also formulated to contain between 0.01 to 0.5 weight percent of L-methionine, e.g., 0.01-0.2 weight percent L-methionine, and this component may also be incorporated into the aqueous phase at a concentration effective to give the desired concentration in the final composition, and a chelating agent such as EDTA or an antioxidant such as L-methionine and/or a protein stabilizer such as glycine.

A. Formation of an Anhydrous Plastic Proliposome Gel

A liposome-forming component and other necessary excipients are melted with a pharmaceutically acceptable hydrophilic solvent, such as propylene glycol.

The expression "liposome-forming component" designates the substance or substances used as major component of the lipid bilayers. Typical liposome-forming components include glycolipids, lecithins, phospholipids, ceramides or mixtures thereof which are used as a primary ingredient in the formation of the lipid bilayer. However, other natural and synthetic compounds having the required amphipatic character can be incorporated with the phospholipid, glycolipid or ceramide, replacing some of these expensive materials, provided that the essential character of the lipid bilayers is not adversely affected. The choice of the appropriate materials is within the knowledge of the person skilled in the art. Examples include phosphatidylethanolamine, lysolecithin, lysophosphatidylethanolamine, phosphatidylserine, phosphatidylinositol, sphingomyelin, cardiolipin, phosphatidic acid and the cerebrosides, ether lipids and phytanols.

The liposomal formulations of the present invention preferably contain saturated and/or unsaturated phospholipids, more preferably phosphatidylcholine, lysophosphatidylcholine, phosphatidylserine, phosphatidylethanolamine, glycolipids and ceramides. The phospholipids are preferably in combination with a penetration enhancing agent such as monolauroyllysine, dipalmitoyllysine or methyl salicylate to achieve predominantly transdermal delivery potential.

A "fatty substance" can be used to enhance the strength of the lipid bilayers. Examples of useful fatty substances include steroids such as cholesterol, coprostanol, cholestanol and cholestane and long chain fatty acids ($C_{16}$ to $C_{22}$), especially saturated ones such as stearic acid. In addition to enhancing strength of the lipid bilayer, acids impart a negative charge. Saturated or unsaturated acids can be used. Other fatty substances that can be used include $C_{16}$ to $C_{22}$ fatty amines, fatty acylated proteins, fatty acylated peptides, fatty acylated PEG and derivatives. These fatty substances are incorporated with the abovementioned liposome-forming components and improve physical stability and appearance of the product.

The hydrophilic solvent is used as a plasticizer of the liposome-forming component and an aid to prepare a uniform melt. Examples of hydrophilic solvents include but are not restricted to propylene glycol, glycerol, polyethylene glycol having a molecular weight ranging between 300 and 8000, ethanol, and mixtures thereof. The resulting melt can be described as being an anhydrous plastic proliposome gel. This anhydrous plastic proliposome gel contains all the lipid phase ingredients and can be prepared and stored in advance in large quantities. It is a semisolid material with a homogenous consistency.

B. Formation of the Multilamellar Lipid Vesicles

Hydrophilic ingredients such as penetration enhancers, preservatives and the like, are prepared separately as an aqueous solution, which forms the continuous phase of an emulsion. This is added to the lipid phase melt, previously heated to the appropriate melting temperature that can range from 40° C. to 80° C., and vigorously mixed by any given technique which allows the achievement of the desired product size. Examples of mixing techniques include vortexing or propeller mixing. At this stage, it is also possible to incorporate (dissolve) solid biologically active agents that will be entrapped within the lipid bilayers.

This procedure is suitable for the preparation of various amounts of topical liposomal product. If vortex mixing is used as the agitation, up to about 20 g of the product can be prepared. If a laboratory scale propeller mixer is used, up to about 2 Kg to 10 Kg of the product can be made. This formulation procedure can also be adapted for large scale manufacturing. Hence, the propeller mixing technique can be directly scaled up by geometrically increasing the size of the vessel and the diameter of the propeller mixer. However, as the vessel size increases, the preferred set up would be a combination mixer i.e a high intensity mixer with propeller mixer and a scraped surface agitator. The aqueous phase can either be pumped from tank A to tank B containing the anhydrous plastic proliposome gel or the aqueous phase can be mixed with the emulsion prior to adding to Tank B at the required temperature and mixed. This procedure is suitable for the production of any topical liposomal product on a large scale.

Liposomal compositions can be prepared with the multilamellar lipid vesicles of the present invention by using appropriate pharmaceutical additives. For example, it might be required to add viscosity increasing agents to the final liposome preparation. The addition of other pharmaceutically acceptable compounds is within the purview of the person skilled in the art.

C. Characteristics of the Final Multilamellar Lipid Vesicle Product

A schematic representation of a multilamellar lipid vesicle prepared in accordance with the process described above is shown at FIG. 3. The multilamellar lipid vesicle, generally designated by reference numeral 2, is made of a series of spaced apart lipid bilayers 4, 6 and 8 which define a series of peripheral aqueous solution compartments 3 and 5. The smallest lipid bilayer 7 defines in its center a central core compartment 9. Although only 6 lipid bilayers are shown, it should be appreciated that the figure is simplified and schematic and in fact many more than 6 lipid bilayers are present.

Figure 3:
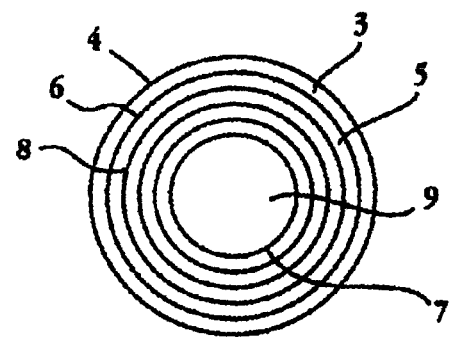
FIG. 3 is a schematic sectional view of a biphasic MLV with a central aqueous emulsion core.
Figure 4:
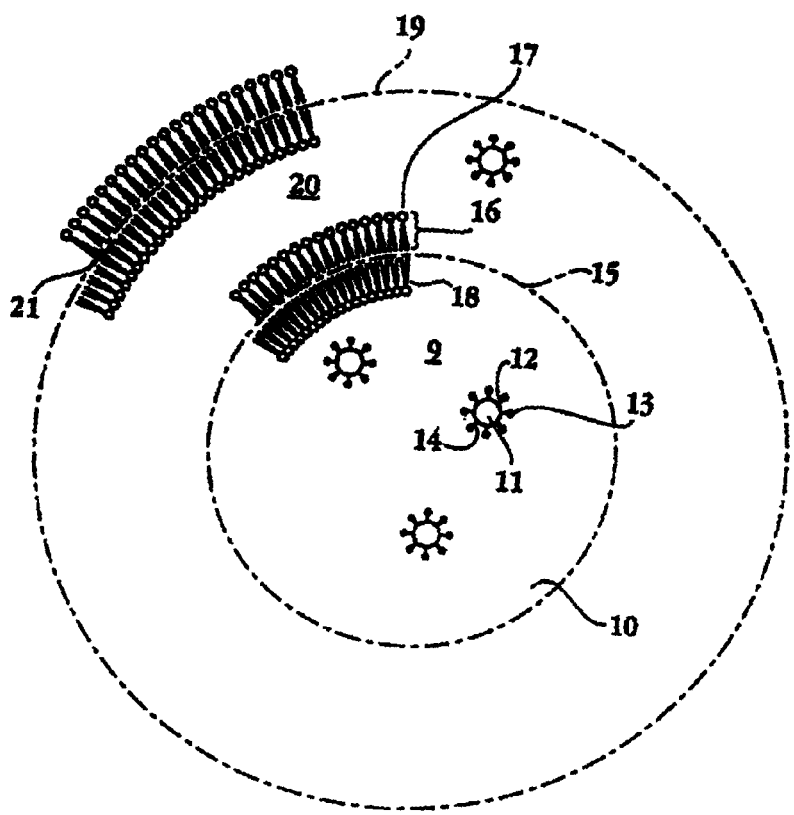
FIG. 4 is an enlarged portion of the MLV of FIG. 3.

FIG. 4 is an enlargement of the vesicle of FIG. 3 showing in more detail the central core compartment and parts of some of the lipid bilayers. The central core compartment 9 is occupied by an aqueous emulsion composed of water 10 as continuous phase and lipophilic droplets or fine solid particles 11 as dispersed phase. The lipophilic droplets or fine solid particles are surrounded by a layer of surfactant molecules 12, the hydrophilic portions 13 of each surfactant molecule extending into the aqueous phase and the hydrophobic portions being at the surface of the oil droplets.

Surrounding the core compartment is the innermost lipid bilayer 15. The lipid bilayer is composed of two layers of lipid molecules 16. Each lipid molecule 16 in a layer is oriented substantially parallel to adjacent lipid bilayers, and two layers that form a bilayer have the polar ends 17 of their molecules exposed to the aqueous phase and the non-polar ends 18 adjacent to each other. Between the innermost lipid bilayer 15 and the next innermost lipid bilayer 19 is a peripheral compartment 20 that is filled either with water or with the aqueous emulsion. As shown, surfactant surrounded lipophilic droplets or particles 11 can be present in the peripheral compartment 20.

Surrounding the peripheral compartment 20 is the next innermost lipid bilayer 19, which is in turn surrounded by a further peripheral compartment and a further lipid bilayer.

It will be appreciated that biologically active ingredient, e.g., interferon alpha-2b, and the L-methionine component will be present in the water of the aqueous emulsion in the central core compartment 9 and in the peripheral compartments 20. Biologically active ingredients that are lipophilic, such as consistency enhancers or uptake enhancers, can be present in the dispersed phase of the emulsion in the central compartment 9 and in the peripheral compartments 20. They can also be present in the interior of the lipid bilayers as shown at 21. The biologically active ingredient can constitute the lipophilic droplets 21, or the biologically active ingredient can be dissolved in a lipophilic solvent that forms droplets 21. Thus the invention permits the topical application of biologically active ingredients that are water-soluble or water-insoluble.

The composition is preferably formed under conditions in which at least about 30 weight percent, and preferably between about 40 and 70 weight percent of these aqueous components is present in liposome entrapped form, as opposed to being carried in the extra-vesicular bulk phase of the composition. These levels of entrapment can be achieved by various known strategies, e.g., forming the lipsomes by a reverse-phase evaporation method and/or encapsulating the aqueous phase material at a high concentration of liposome-forming lipids, thus minimizing the amount of bulk aqueous phase.

FIG. 1 is a scanned image, magnified 440× of vesicles made for use as a topical lotion. This product displayed the consistency of a lotion or semi-solid cream. Inspection of the scanned image reveals multilamellar structures with uniform size distribution. These have displayed physical stability for extended periods of time of more than one year.

Figure 2A:
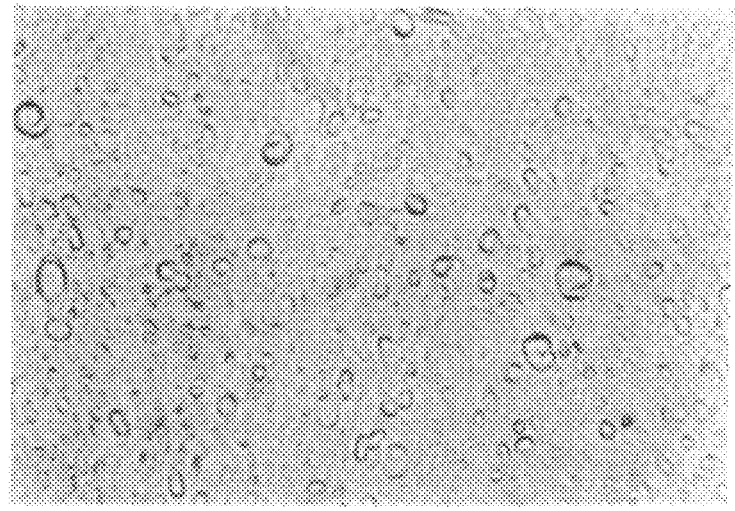
FIG. 2A is a scanned image of multilamellar liposomes prepared using an "anhydrous plastic proliposome-gel" ('melt' or 'fusion') method.
Figure 2B:
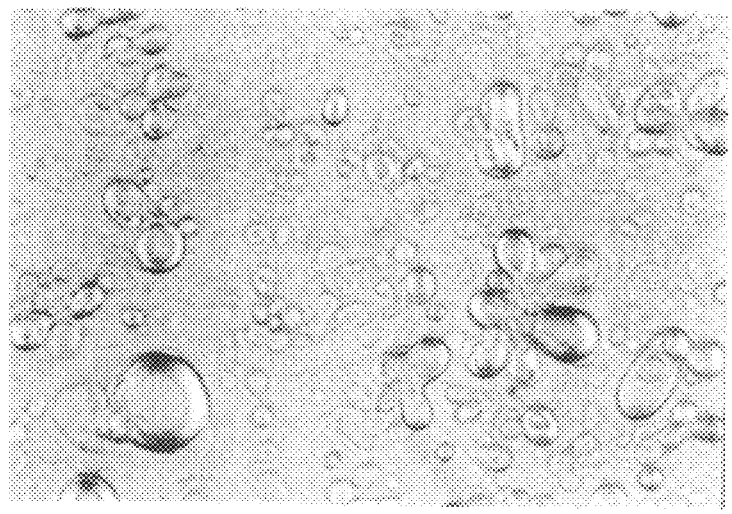
FIG. 2B is a scanned image of multilamellar liposomes the same composition as in 2A, but prepared by a solvent evaporation method.

In order to demonstrate the difference in properties observed in the liposome population produced in accordance with the preferred method of the present invention, comparative tests were conducted between two liposome compositions prepared from the same ingredients but using in one case the solvent evaporation method and in the other case the preferred anhydrous plastic proliposome gel method. FIG. 2A is a scanned image of the liposome population prepared using the anhydrous proliposome gel ('melt' or 'fusion') method and FIG. 2B is a scanned image of the liposome population prepared using the solvent evaporation method. As can be seen, the liposome population obtained using the anhydrous plastic proliposome gel method has a liposome size distribution which is substantially more uniform than that obtained using the solvent evaporation method. Also, minimal amounts of aggregated or fused liposomes are formed when using the anhydrous plastic proliposome gel method, whereas large aggregates can be observed in the liposome population obtained using the solvent evaporation method.

In some embodiments of the invention the lipophilic substance is an oil or solid/semisolid lipophilic consistency enhancer which can be encapsulated into liposomes. As solid or semisolid lipophilic consistency enhancers there are mentioned fatty alcohols, waxes, fatty alcohol fatty acid esters, glyceride esters, white petrolatum and mixtures thereof. Examples of oils which have successfully been encapsulated into liposomes pentaerythritol tetracaprylate/caprate, pentaerythritol tetraisostearate, cetearyl octanoate and canola oil, jojoba oil, peanut oil, rice bran oil, cottonseed oil, sunflower oil, corn oil, walnut oil, avocado oil, peru balsam, clove oil and eugenol. Plant extracts based on oil have also been successfully incorporated into liposomes. Solid/semi solid lipophilic consistency enhancer ingredients can be selected from waxes, fatty alcohols, fatty acid esters, glyceryl stearate, petrolatum or combinations thereof. Specific examples of preferred consistency enhancers include beeswax, glyceryl tribehenate, glyceryl stearate, stearyl heptanoate, stearyl palmitate, cetyl alcohol, stearyl alcohol, myristyl myristate, behenyl erucate and cetyl palmitate.

The viscosity of a composition of vesicles in accordance with the invention and containing a consistency enhancer is greater than the viscosity of corresponding vesicles that do not include a consistency enhancer but are otherwise identical. By varying the amount of consistency enhancer it is possible to achieve virtually any required viscosity, from a relatively mobile liquid, to a "lotion", to "creamy" to "thick cream". Determination of amounts of consistency enhancer to achieve a particular viscosity of the composition can be determined by routine experiment.

The surfactant used to coat the oil droplet or the solid/semisolid lipophilic consistency enhancer ingredients is important for the successful encapsulation of a lipophilic core into multilamellar lipid vesicles. About 30 different types of surfactants were screened and primary cationic emulsifiers were found to give the most acceptable results. The most preferred surfactant is benzalkonium chloride. Nonionic or amphoteric surfactants can also be used, such as naturally derived emulsifiers: PEG-60 almond glycerides, avocado oil diethanolamine, ethoxylated jojoba oil (PEG-40 Jojoba acid and PEG-40 Jojoba alcohol); polyoxyethylene derivatives: polyoxyethylene (20) sorbitan monooleate, polyoxyethylene (20) sorbitan monostearate; lanolin derivatives: polychol 20 (Laneth 20), polychol 40 (laneth 40); neutral phosphate esters: PPG-cetyl ether phosphate, DEA oleth-3 phosphate. It is also possible to use anionic surfactants such as acyl-glutamates: TEA-cocoyl glutamate, sodium lauroyl glutamate, sodium hydrogenated tallow glutamate and sodium cocoyl glutamate. It is desirable that the surfactant has a high critical micellar concentration (CMC).

When preparing the lipophilic substance-in-water emulsion, the hydrophilic ingredients and surfactants are all incorporated in water. Once the water phase of the emulsion has been prepared, the oil and/or solid/semisolid lipophilic ingredients are added to the water in a homogenizer for a period of time ranging from 5 to 30 minutes to obtain relatively small droplet size. Preferred droplet size ranges from 0.1 um to 1 um, most preferably below about 0.5 um. The lipid phase melt is then heated and the lipophilic substance-in-water emulsion is added and vigorously mixed by either vortexing or propeller mixing depending on the product size.

The formulation procedure described above can be easily adopted for large scale manufacturing. The propeller mixing approach can be directly scaled up by geometrically increasing the size of the vessel and the diameter of the propeller mixer. However, as the vessel size increases, a preferred set up might be a combination mixer such as a high intensity mixer with propeller mixer and a scraped surface agitator. In a large scale operation, the lipophilic substance-in-water emulsion can be pumped from a first tank into a second tank containing the anhydrous plastic proliposome gel at the required temperature and mixed.

With the multilamellar lipid vesicle of the present invention, oil droplets containing solubilized lipophilic biologically active compounds or oily plant extracts can be delivered through liposome encapsulation. Furthermore, the possibility of multicompartment encapsulation provides drug release over extended periods of time. Also, encapsulation of lipophilic solid/semisolid consistency enhancers into the central lipophilic core compartment provides enhanced viscosity to the final liposome composition. In this case, the addition of viscosity-increasing agents in the final liposome preparation can be avoided.

Overall, the preparation of multilamellar lipid vesicles with a central emulsion core component provides a physically stable, uniform liposome composition. The composition has a viscosity that is suitable for topical administration and can be easily manufactured on a large scale.

D. Exemplary IFN-alpha-2b Cream Formulation for Intravaginal Use

Table 1 gives the components in one exemplary lipid-bilayer composition formed in accordance with the invention, where the amount of each component is expressed in units of mg/g final composition, and given in both ranges and exemplary quantities (parentheses). The resulting composition is referred to in the studies below as "Formulation Q25C", and is formed as detailed below.

TABLE 1

| Component | Quantity mg/g |
|---|---|
| Active | |
| Interferon alpha-2b Drug Substance | .01-5 (0.808) |
| Excipients and protective agents | |
| Benzalkonium Chloride 50% Solution | 1-10 (2) |
| Butylated Hydroxytoluene | 0.1-0.5 (0.102) |
| Cetyl Alcohol | 2-40 (20.514) |
| Cholesterol | 2-40 (20) |
| Edetate Disodium Dihydrate | 0.1-0.5 (0.103) |
| Glycerol Monostearate 40-55, Type 1 | 5-50 (30.771) |
| Glycine | 0.1-5 (1) |
| L-Methionine | 0.1-5 (1.126) |
| Methylparaben | 0.1-5 (1.538) |
| Olive Oil, Super Refined | 10-70 (51.285) |
| PEG-40 Castor Oil, Hydrogenated | 10-70 (51.285) |
| Sodium phosphate, Dibasic, Heptahydrate | 1-2 (1.670) |
| Sodium phosphate, Monobasic, anhydrous | 0.25-1 (0.480) |
| Phospholipon 90H | 60-200 (100) |
| Propylene Glycol | 30-100 (69.95) |
| Propylparaben | 0.1-1 (0.513) |
| Purified Water | Q.S. to 1000 (646.846) |

Description of the Manufacturing Process for Q25C

Step 1. Preparation of oil-in-water microemulsion: Olive oil, glycerol monostearate 40-55 Type I, cetyl alcohol and butylated hydroxy toluene are melted together at 75° C.±5° C. The aqueous component of the emulsion including purified water, PEG-40 castor oil hydrogenated, benzalkonium chloride 50% solution, methylparaben, propylparaben, L-methionine, edetate disodium dihydrate, and phosphates are heated together in a stainless steel vessel at 75° C.±5° C. while stirring until the ingredients are dissolved. The oil component (75° C.±5° C.) is then added to the aqueous component (75° C.±5° C.) gradually, while mixing to form a coarse emulsion. Coarse emulsion is then homogenized by processing through a Microfluidizer until a homogeneous emulsion is formed. This microemulsion is cooled down to 8° C.-12° C.

Step 2: Preparation of the Lipid Phase: The Lipid Phase is prepared by melting Phospholipon 90H, cholesterol and butylated hydroxy toluene with propylene glycol in a MMU 10 mixer by heating to about 80-90° C. while mixing at a slow speed. The mixing and heating of the Lipid Phase ingredients is continued until a clear melt is formed which is then cooled to about 60° C.

Step 3: Preparation of the Aqueous Phase: The required quantity of IFN alpha-2b stock solution is added and mixed gently with a mixture of L-methionine, glycine and purified water.

Step 4: Product Formulation: The Aqueous Phase containing interferon alpha-2b (from Step 3) is added to the System A (from Step 1) in a stainless steel jacketed mixing tank. This mixture is maintained between 8° C.-12° C. while the mixture is mixed slowly and purged with nitrogen gas. The cooled mixture of System A-Aqueous Phase is rapidly added to the Lipid Phase which is being mixed at high speed in the MMU10 mixer. Mixing proceeds for 10-15 minutes while the temperature of the mixture is maintained about 57-60° C. The bulk product thus formed is slowly mixed and cooled to 19° C.-25° C. in a MMU 10 mixer. The product is transferred from the MMU 10 mixer into a 10 L stainless steel storage vessel and purged with nitrogen gas. The bulk product is filled into 1 g polypropylene tubes using a Unipac 100 Filler. The tubes are purged with nitrogen and then the required amount of the product is filled into the tubes, which are thermally sealed. The filled tubes of Interferon alpha-2b Cream are stored at 5° C.±3° C.

II. Preclinical and Clinical Studies on Efficacy Against LSIL

A. Study Rationale

At present, there is no immediate therapy available for women with HPV presenting with LSIL. Interferon is known to be active against a variety of HPV-induced lesions, particularly cutaneous lesions, such as genital warts. A therapy that could treat early stage cervical HPV infections would provide a significant benefit to and the physical and emotional well-being of many young women.

B. Summary of Pre-Clinical Studies with Q25C

Toxicology studies conducted in support of the present invention were conducted in compliance with the requirements of "Good Laboratory Practice for Nonclinical Laboratory Studies" and OECD Principles of Good Laboratory Practice. The following three types of toxicology studies were carried out:

Skin sensitisation of Topical Interferon Alpha-2b Cream in guinea pigs (Buehler Method).

Repeated dose dermal irritation study of Topical Biphasix Interferon Alpha-2b Cream in rabbits.

Vaginal irritation study of Interferon Alpha-2b Cream in rabbits.

Apart from the 3 above mentioned toxicology studies, the following should be taken into account for the toxicology profile for IFN-alpha-2b composition of the invention: The active drug substance, interferon alpha-2b, is widely considered a safe drug therapy as marketed world-wide by the supplier of the drug substance, Schering Plough (Intron A®). Intron A® is a purified recombinant DNA copy of naturally occurring Interferon-alpha-2b, and has a specific activity of interferon alpha-2b of approximately $2.6 \times 10^8$ IU/mg protein as measure by HPLC assay.

Schering Plough has already completed extensive toxicology profiling with interferon alpha-2b in multiple species.

The patent owner performed the clinical trial described herein such that daily and total interferon alpha-2b administration to patients did not exceed published safety limits.

The components making up the composition are all quality, recognized ingredients.

The pre-clinical profiling has included two formulations of Interferon alpha-2b Cream designated "Formulation Q25C" whose composition and method of preparation are described above.

B1. Skin Sensitization Studies

A 10-day exploratory study was performed in which Formulation Q25C was applied twice daily to sites on shaven skin of the dorsal aspect of New Zealand Albino rabbits at a concentration of 2 MIU interferon alpha-2b per gram of cream (1× the proposed clinical concentration). Test sites were cleaned in between applications using the moistened gauze technique described above to remove any residual cream from previous applications. Study controls included a negative control (saline) and a vehicle control (identical in composition to Formulation Q25C, minus interferon alpha-2b replaced with additional Purified Water).

The appearance of skin sites was rated and scored for signs of erythema and oedema daily using the standard Draize scoring system. In addition, animals were observed daily for any sign of systemic toxicity. No necropsy assessments were performed at the end of the study.

Through the course of this exploratory study, findings for erythema were generally good, (Draize scores for redness of generally 2), and only very slight or slight oedema (score of 1-2) was observed. Most notably, skin fissures present on intact surfaces were apparent in one animal only. No signs of systemic toxicity were observed.

C. Vaginal Irritation Studies

Formulation Q25A was administered intravaginally daily for 5 consecutive days/week for 6 weeks at concentrations of 2 MIU and 20 MIU interferon alpha-2b per gram of cream (1× and 10× the proposed clinical concentration). Study controls included a negative control (saline) and a vehicle control minus interferon (alpha-2b replaced with additional Purified Water).

The appearance of the vaginal opening and perineum was rated for signs of erythema, oedema and vaginal discharge daily. In addition animals were observed daily for any signs of systemic toxicity, and sacrificed at the end of the study to determine any signs of gross pathology.

The rabbits did not show evidence of systemic toxicity or vaginal irritation based on in-life observations of the vaginal opening and perineum during the study. At necropsy, no gross pathological findings were noted in tissues/organs (including vagina). Based on the histopathology grading, the cream was classified as a minimal irritant.

Minimal to mild vaginal epithelial hyperplasia, metaplasia and large vacuolation of the epithelium or lamina propria were observed in several animals to whom vehicle control cream was administered and in 1 saline control animal. Hyperplasia and metaplasia may represent minimal to mild adaptive epithelial responses to repeated daily administration of the vehical cream over the 6-week study duration. There was no vaginal epithelial necrosis, erosion or ulceration present in any animals.

Conclusions from Toxicology Studies To-Date

The above studies support the conclusion that the composition of the present invention, as embodied in Formulation Q25C, is non-sensitizing, and at worst, a mild to moderate irritant for a transient period initially and, thereafter, only mildly irritating, if at all, through the 30-day period studied.

D. Clinical Studies

The composition of the present invention, as embodied in the Q25C Formulation, was tested for clinical efficacy and side effects in the treatment of LSIL with HPV status, (Low-Grade Squamous Intraepithelial Lesion with human papaloma virus status), where "intraepithelial" means abnormal cells are only present in the surface layer of the cervix. The objective of the study was to determine efficacy and safety of the application of topical Interferon alpha-2b Cream Q25C compared with a second study performed as a control population to describe the natural history of disease progression or regression. The methodology and clinical study, number of subject studies, and the clinical endpoints are presented in Table 2, and the criteria for evaluation, in Table 3.

TABLE 2

Clinical Trial summary: Low dose interferon alpha cream for the treatment of cytologically confirmed LSIL with HPV status

| | |
|---|---|
| Investigated product: | IFN002: topical Interferon alpha-2b Cream<br>HPV001: no treatment |
| Title of studies: | Protocol Number: IFN 002 - An open study of topical Interferon alpha-2b Cream for the treatment of cytologically confirmed LSIL with HPV status (Phase II)<br>Protocol Number: HPV001 - A 3-month prospective study of women presenting with cytologically confirmed LSIL with HPV+ status - a non interventional study |
| Investigator(s): | Principal Investigators:<br>IFN002: Prof. Dr. med. Achim Schneider, Germany<br>HPV001: Dr. med. Gerd Bohmer, Germany |
| Study centre(s): | IFN002: 3 centers in Germany<br>HPV001: 1 center in Germany |
| Objectives: | IFN 002: To determine efficacy and safety of the application of topical Interferon alpha-2b Cream<br>HPV001: To describe the natural history of disease progression or regression |
| Methodology: | IFN 002: Prospective, open labeled study with 6 weeks of treatment and a 6 week follow-up observation period<br>HPV001: Prospective single cohort study with a 12 week observation period |

| | | IFN002 (treatment) | HPV001 (control) |
|---|---|---|---|
| Total number of subjects (planned and analyzed): | Planned for PP | 20 | 20 |
| | Enrolled/Screened* | 78 | 38 |
| | Safety analysis | 20 | 21 |
| | ITT-Analysis | 20 | 21 |
| | PP-Analysis | 15 | 19 |

| | |
|---|---|
| Diagnosis and main criteria for inclusion: | Both studies: Women presenting with cytologically confirmed LSIL with HPV+ status |
| Kind and duration of treatment: | IFN 002: topical Interferon alpha-2b Cream for 6 weeks<br>HPV001: no treatment |
| Criteria for evaluation: | |
| Efficacy: | Primary endpoint:<br>IFN002: PAP-response-rate, defined as the proportion of patients with resolution of an abnormal Pap smear during 12 weeks after the start of the treatment period (i.e. week 2 or 4 or 6 or 12 = visit V04, V05, V06 and V07) in the Intention to Treat population (ITT)<br>HPV001: proportion of patients with resolution of an abnormal Pap smear at the end of the 12 weeks observation period.<br>Secondary endpoints:<br>Same as the primary endpoint for Per Protocol population (PP), however<br>Proportion of patients with reversion of HPV+ Status to negative (qualitative assessment) during 12 weeks after the start of the observation period (ITT and PP)<br>Proportion of patients with quantitative reduction of HPV viral load during 12 weeks after the start of the observation period (ITT) |
| Safety: | Adverse events<br>Safety laboratory tests<br>Vital parameters |

TABLE 3

| | |
|---|---|
| Statistical methods: | Efficacy parameters: Inferential statistical analysis of the efficacy parameters was purely explorative, using $\alpha = 0.05$ for each test carried out without $\alpha$-adjustment for multiple testing. The difference in response rates between both groups was determined with the $Chi^2$-test.<br>Safety parameters: All analyses were of descriptive nature. Laboratory parameters were analyzed by means of the asymptotic Mann-Whitney-U-test (between groups differences) and the asymptotic Wilcoxon-test for dependent samples (within group differences). All AEs were coded according to MedDRA and listed completely and separately by study groups. An AE related and a patient related analysis was performed. |
| Main efficacy | Primary endpoint (ITT): 8 out of 20 patients (40.00%) in the |

TABLE 3-continued

| | |
|---|---|
| results: | treatment-group were responders compared to 3 out of 21 patients (14.29%) in the control-group. However, Pap smear results of two patients of the treatment group worsened after a preliminary PAP-response at earlier visits. Thus, if one considers PAP-response after the 12 week observation period only, 6 out of 20 patients (30.00%) of the treatment group were responders. PAP-response in the Per Protocol population (PP): In the treatment-group 7 out of 15 patients (46.67%) were responders compared to 3 out of 19 patients (15.79%) in the control-group. If one considers PAP-response after the 12 week observation period only, 6 out of 15 patients (40.00%) of the treatment group were responders.<br>Proportion of patients with resolution of HPV+ status (ITT and PP) during 12 weeks treatment period, i.e. patients with an occurrence of HPV-at least one time after V03 = start of treatment). ITT: In the treatment-group 3 out of 20 patients (15.00%) were HPV-responders in contrast to 2 out of 21 patients (9.52%) in the control-group. Comment: the HPV-status of one treatment-group patient worsened at V06, but it was negative again at visit V07. PP: In the treatment-group 2 out of 15 patients (13.33%) were HPV-responders and 2 out of 19 patients (10.53%) in the control-group. |
| Additional efficacy results | Pap-response from a stratified population of patients entering the study as PAP IIID only (i.e., per "The Bethesda Classification System" of LSIL cytology). A subgroup analysis of the PAP IIId presenting patients revealed a significant difference between treatment groups. 6 of the 14 PAP IIId patients from the ITT-population of study IFN002 were responders compared to no responder in the 14 PAP IIId patients from the PP-population. Colposcopic diagnosis. The colposcopic diagnosis was statistically significantly better in the treatment group compared to the control group at the time of individual final observation. In study IFN 002, 12 patients (60%) improved towards 'normal' or atypical'. By comparison, in the non-interventional study, only 2 patients (9.52%) improved at the time of individual final observation |
| Main safety results: | Adverse events: 36 AEs were documented. 34 AEs in the treatment-group: 7 of these onset before start of treatment. Two SAEs were observed in 1 patient of the control group. AE analyses were based on the 27 AEs of the treatment group which started after start of treatment ('treatment emergent AEs'); these 27 AEs occurred in 14 of 20 patients (70.00%) of the treatment-group. According to MedDRA-primary terms 3 AEs came from the category 'Metrorrhagia' and 4 from the category 'Headache'; all other AEs-classes occurred only once or twice. 5 SAEs in 3 patients all without any causal relationship related to treatment occurred under study medication (treatment group: pregnancy before start of treatment in 1 patient, accident during swimming with concussion of the brain and compression of the cervical spine in 1 patient; control group: pregnancy with abortion in 1 patient). There were no deaths and no other significant AEs. Laboratory: Urine: No significant change over time was observed with respect to urine-pH-values. In one center, some urine parameters were determined quantitatively: while there was a clear increase of mean erythrocytes, pre-post-changes were small and not significant for this and the other parameters. In some patients qualitative determined leucocytes, nitrate, protein, urobilinogen, bilirubin and/or blood were found in urine. Blood: Significant between group differences were found with respect to hematocrit, MCV, MCHC, thrombocytes and basophils at start and end of the study, not, however, with respect to the mean pre-post-changes. There seems to be a tendency for an increase in leucocytes (however, not significant), lymphocytes [Gpt/I] (significant), monocytes [Gpt/I] (significant) and basophils [Gpt/I] (significant) in the treatment group patients. Significant between group differences were found with respect to creatinine, ASAT and alkaline phosphatase (AP) at start and end of the study, not, however, with respect to the mean pre-post-changes. There was a significant mean decrease with respect to bilirubin in both groups, and a significant mean increase with respect to ALAT in the control group. For all lab parameters addressed in the CRF, the Investigator's assessment (normal, if outside normal range: clinically relevant or clinically irrelevant) was required. Clinically relevance was documented in a rare number of cases only Physical examination and vital signs: Only in one case from the treatment-group a pathological finding was observed at visit V06 (angina). Within each study group, the vital signs remained nearly constant during the trial within the limits of normal fluctuation and measurement errors. There was a significant difference between groups (U-tests) with respect to diastolic blood pressure and heart rate at visit V01 with higher values in the treatment-group, but no significant difference with respect to the pre-post-differences. |

TABLE 3-continued

| | |
|---|---|
| Conclusions: | Overall the treatment arm has a higher response rate than the untreated compare group. Statistic significance using α = 0.05 is not met for the primary endpoint if compared directly. However, the small sample size and the fact the studies were conducted separately and independently with slightly different colposcopic examination schedules make this type of comparison difficult.<br>A subgroup analysis of the PAP IIId presenting patients revealed a significant difference between treatment groups. 6 of the 14 PAP IIId patients from the ITT-population of study IFN002 were responders compared to no responder in the 14 PAP IIId patients from the PP-population.<br>The colposcopic diagnosis was statistically significantly better in the treatment group compared to the control group at the time of individual final observation. In study IFN 002, 12 patients (60%) improved towards 'normal' or atypical'. By comparison, in the non-interventional study, only 2 patients (9.52%) improved at the time of individual final observation.<br>None of the SAEs was related to the study drug and no other significant AEs occurred. The treatment shows an excellent safety profile.<br>A potential clinical benefit and the lack of significant drug related adverse events are positive indications for the drug tested. |

Efficacy parameters: Inferential statistical analysis of the efficacy parameters was purely explorative, using α=0.05 for each test carried out without α-adjustment for multiple testing. The difference in response rates between both groups was determined with the Chi$^2$-test.

The main study outcome was based on the Pap-response rate as compared between the two study populations. Pap smear normalization was considered to occur if the patient's Pap smear improved to group II or better from any of Pap smear groups IIW through IIID as per the common European or "Munich Classification" system of LSIL cytology.

Safety parameters: All analyses were of descriptive nature. Laboratory parameters were analyzed by means of the asymptotic Mann-Whitney-U-test (between groups differences) and the asymptotic Wilcoxon-test for dependent samples (within group differences). All AEs were coded according to MedDRA and listed completely and separately by study groups. An AE related and a patient related analysis was performed.

Primary endpoint (ITT): 8 out of 20 patients (40.00%) in the treatment-group were responders compared to 3 out of 21 patients (14.29%) in the control-group. However, Pap smear results of two patients of the treatment group worsened after a preliminary PAP-response at earlier visits. Thus, if one considers PAP-response after the 12 weeks observation period only (as by definition in the control group), 6 out of 20 patients (30.00%) of the treatment group were responders.

PAP-response in the Per Protocol population (PP: In the treatment-group 7 out of 15 patients (46.67%) were responders compared to 3 out of 19 patients (15.79%) in the control-group. If one considers PAP-response after the 12 weeks observation period only Adverse events: 36 AEs were documented. 34 AEs in the treatment-group: 7 of these onset before start of treatment. Two SAEs were observed in 1 patient of the control group. AE analyses were based on the 27 AEs of the treatment group which started after start of treatment ('treatment emergent AEs'); these 27 AEs occurred in 14 of 20 patients (70.00%) of the treatment-group. According to MedDRA-primary terms 3 AEs came from the category 'Metrorrhagia' and 4 from the category 'Headache'; all other AEs-classes occurred only once or twice. 5 SAEs in 3 patients all without any causal relationship related to treatment occurred under study medication (treatment group: pregnancy before start of treatment in 1 patient, accident during swimming with concussion of the brain and compression of the cervical spine in 1 patient; control group: pregnancy with abortion in 1 patient). There were no deaths and no other significant AEs.

Laboratory: Urine: No significant change over time was observed with respect to urine-pH-values. In one center, some urine parameters were determined quantitatively: while there was a clear increase of mean erythrocytes, pre-post-changes were small and not significant for this and the other parameters. In some patients qualitative determined leucocytes, nitrate, protein, urobilinogen, bilirubin and/or blood were found in urine. Blood: Significant between group differences were found with respect to hematocrit, MCV, MCHC, thrombocytes and basophils at start and end of the study, not, however, with respect to the mean pre-post-changes. There seems to be a tendency for an increase in leucocytes (however, not significant), lymphocytes [Gpt/l] (significant), monocytes [Gpt/l] (significant) and basophils [Gpt/l] (significant) in the treatment group patients. Significant between group differences were found with respect to creatinine, ASAT and alkaline phosphatase (AP) at start and end of the study, not, however, with respect to the mean pre-post-changes. There was a significant mean decrease with respect to bilirubin in both groups, and a significant mean increase with respect to ALAT in the control group. For all lab parameters addressed in the CRF, the Investigator's assessment (normal, if outside normal range: clinically relevant or clinically irrelevant) was required. Clinically relevance was documented in a rare number of cases only.

Physical examination and vital signs: Only in one case from the treatment-group a pathological finding was observed at visit V06 (angina). Within each study group, the vital signs remained nearly constant during the trial within the limits of normal fluctuation and measurement errors. There was a significant difference between groups (U-tests) with respect to diastolic blood pressure and heart rate at visit V01 with higher values in the treatment-group, but no significant difference with respect to the pre-post-differences.

Overall the treatment arm has a higher response rate than the untreated compare group. Statistic significance using α=0.05 is not met for the primary endpoint if compared directly. However, the small sample size and the fact the studies were conducted separately and independently with slightly different colposcopic examination schedules make this type of comparison difficult.

Additional Efficacy Results: A subgroup analysis of the PAP IIId presenting patients revealed a significant difference between treatment groups. 6 of the 14 PAP IIId patients from the ITT-population of study IFN002 were responders compared to no responder in the 14 PAP IIId patients from the PP-population.

Beyond the PAP-response rate parameter, the colposcopic diagnosis was statistically significantly better in the treatment group compared to the control group at the time of individual final observation. In study IFN 002, 12 patients (60%) improved towards 'normal' or atypical'. By comparison, in the non-interventional study, only 2 patients (9.52%) improved at the time of individual final observation.

Although the invention has been described with respect to particular embodiments, it will be apparent to those skilled in the art that various changes and modifications can be made without departing from the invention.

It is claimed:

1. A biphasic vesicle composition comprising:

(a) a first phase comprising an oil-in-water emulsion which itself comprises oil, water, interferon alpha-2b and methionine; and (b) a second phase comprising multilamellar lipid vesicles suspended in said first phase wherein said vesicles contain entrapped therein a composition comprising an oil-in-water emulsion which itself comprises oil, water, interferon alpha-2b and methionine, wherein each phase comprises an amount sufficient of methionine to stabilize said interferon alpha-2b against oxidation, wherein said methionine is the amino acid methionine of the chemical structure:

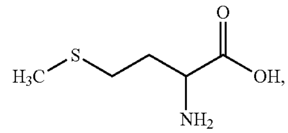

and further wherein said composition comprises a therapeutically effective aggregate amount of said interferon alpha-2b.

2. The biphasic vesicle composition of claim 1, wherein said oil-in-water emulsion is comprised of oil droplets having a size of from about 0.1 μm to 1 μm.

3. A biphasic vesicle composition of claim 1, wherein said methionine is present in a concentration of from 0.01 to 0.5 weight percent.

4. The biphasic vesicle composition of claim 1, wherein at least 30% of said interferon alpha-2b and said methionine is entrapped within said vesicles as part of said oil-in-water emulsion.

5. The biphasic vesicle composition of claim 2, wherein at least 30% of said interferon alpha-2b and said methionine is entrapped within said vesicles as part of said oil-in-water emulsion.

6. The biphasic vesicle composition of claim 3, wherein at least 30% of said interferon alpha-2b and said methionine is entrapped within said vesicles as part of said oil-in-water emulsion.

7. The biphasic composition of claim 1, wherein said multilamellar vesicle comprises from about 2 to about 4 weight percent cholesterol.

8. The biphasic composition of claim 1, wherein said methionine used in each phase is L-methionine.

9. The biphasic composition of claim 1, wherein said interferon alpha-2b is human interferon alpha-2b.

* * * * *